United States Patent [19]

Plaza

[11] Patent Number: 5,133,716
[45] Date of Patent: Jul. 28, 1992

[54] DEVICE FOR CORRECTION OF SPINAL DEFORMITIES

[75] Inventor: Carlos L. Plaza, Montevideo, Uruguay

[73] Assignee: Codespi Corporation, Miami, Fla.

[21] Appl. No.: 610,098

[22] Filed: Nov. 7, 1990

[51] Int. Cl.⁵ .................................... A61F 5/01
[52] U.S. Cl. ............................... 606/61; 606/60
[58] Field of Search ............... 128/69; 606/60, 61, 606/72

[56] References Cited

U.S. PATENT DOCUMENTS

| | | | |
|---|---|---|---|
| 4,269,178 | 5/1981 | Keene | 128/69 |
| 4,641,636 | 2/1987 | Cotrel | 606/61 |
| 4,686,970 | 8/1987 | Dove et al. | |
| 4,738,251 | 4/1988 | Plaza . | |
| 4,773,402 | 9/1988 | Asher et al. | 128/69 |
| 4,875,471 | 10/1989 | Plaza . | |
| 4,998,936 | 3/1991 | Mehdian | 606/61 |
| 5,084,049 | 1/1992 | Asher et al. | 606/61 |

FOREIGN PATENT DOCUMENTS

| | | | |
|---|---|---|---|
| 441932 | 12/1974 | U.S.S.R. | 128/69 |
| 556793 | 6/1977 | U.S.S.R. | 128/69 |
| 624615 | 9/1978 | U.S.S.R. | 128/69 |
| 1063404 | 12/1983 | U.S.S.R. . | |
| 2208476 | 4/1989 | United Kingdom | 606/61 |

OTHER PUBLICATIONS

LUQUE Segmental Spinal Instrumentation.

Primary Examiner—Robert Bahr
Assistant Examiner—Linda C. M. Dvorak
Attorney, Agent, or Firm—Dowell & Dowell

[57] ABSTRACT

An adjustable implant for correcting spinal deformities which includes a frame to which the vertebrae are wired and which frame includes a pair of elongated rod members which are united at spaced intervals by arcuately shaped spacer members which retain the rod members substantially parallel and wherein at least the uppermost spacer member is adjustable along the length of the rod members and selectively lockable with respect thereto. In a modified embodiment one or more spacer members are designed to be movable along curved segments of the rod members.

12 Claims, 4 Drawing Sheets

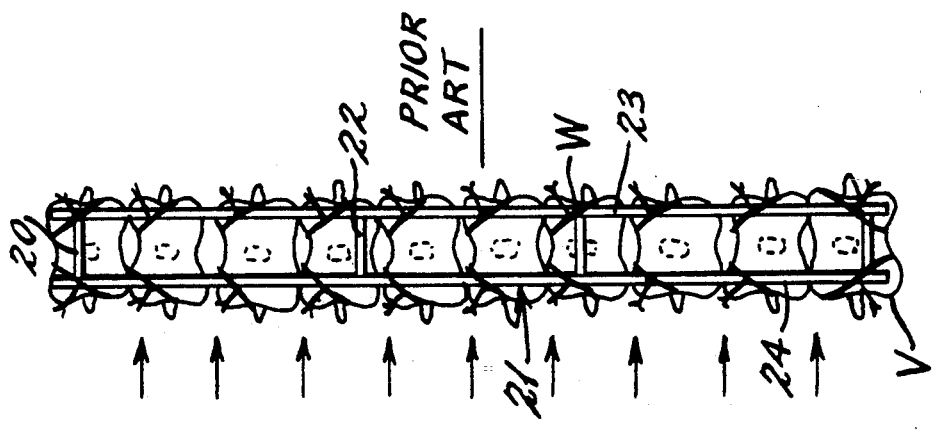
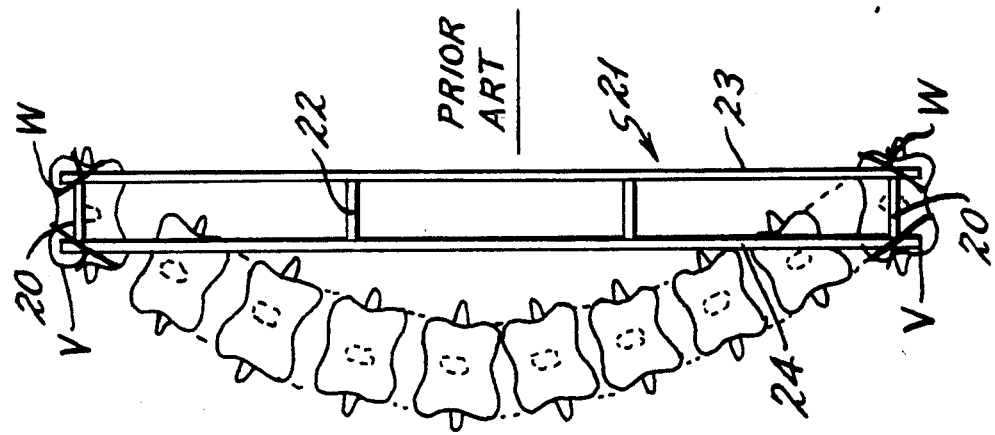
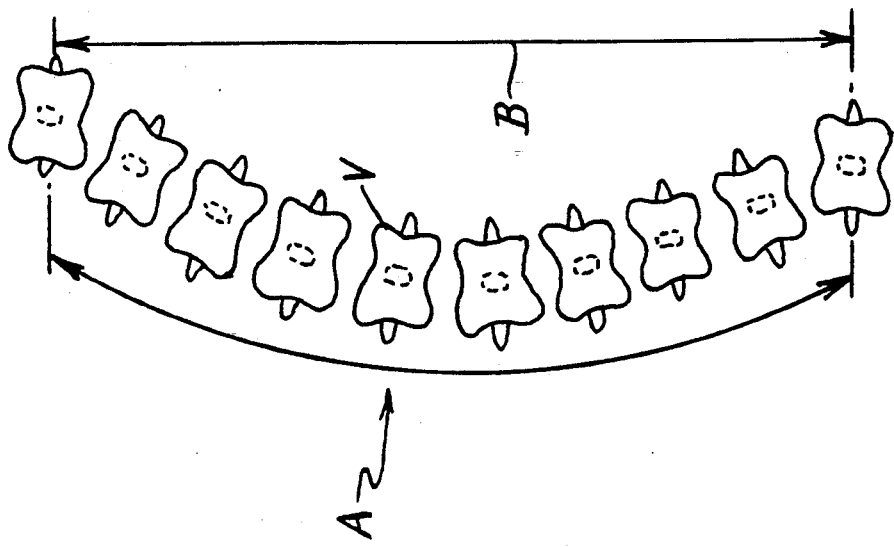

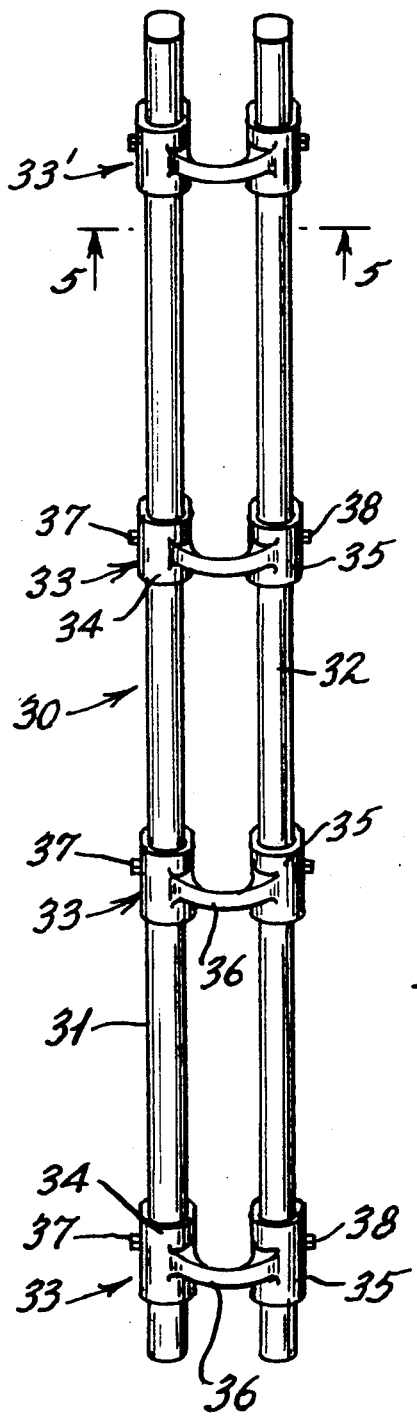
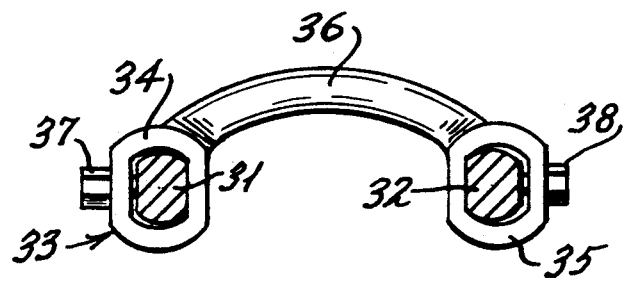
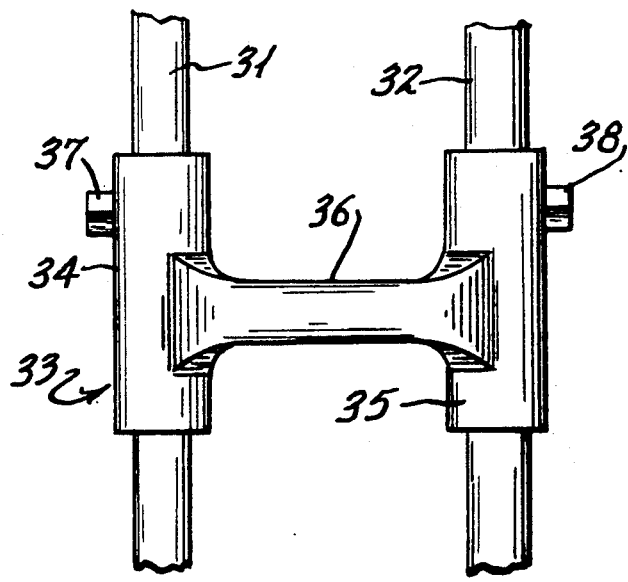

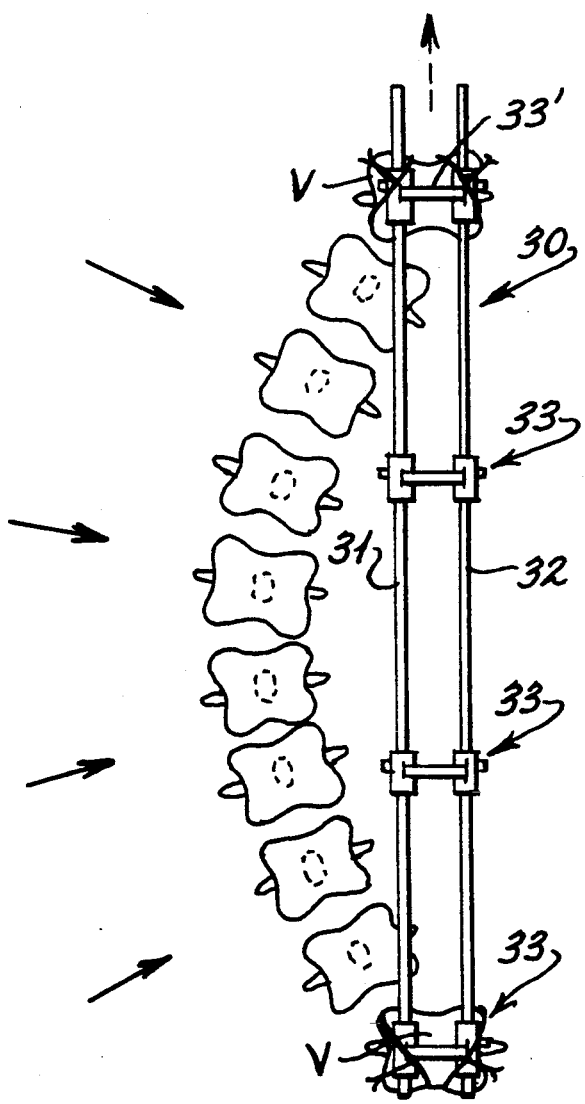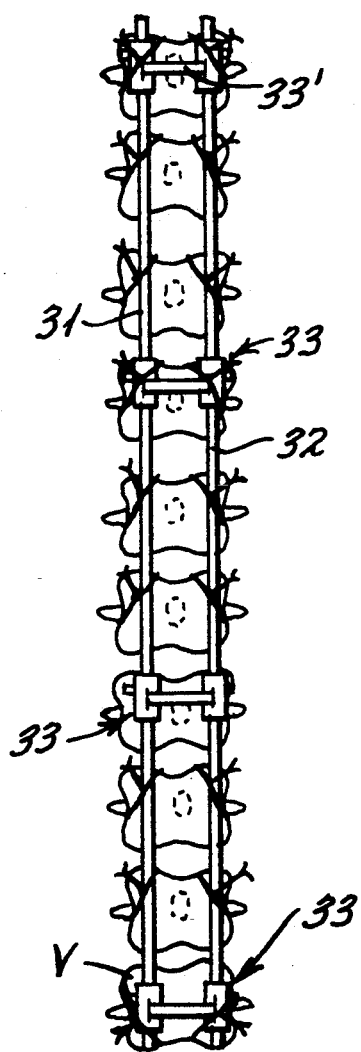

DEVICE FOR CORRECTION OF SPINAL DEFORMITIES

BACKGROUND OF THE INVENTION

1. Field of the Invention

This invention is generally directed to medical implant devices and more specifically to implant devices which are specifically designed for the treatment of scoliosis and wherein the devices include a pair of generally parallel rod members which are reinforced by cross or spacer members that are adjustable to permit varied spacing between the spacer members to thereby both facilitate the placement of the implant and the surgical wiring of the implant to the patient's vertebrae and wherein the spacer members are positively retained in adjusted relationship with respect to the rod members after being adjusted along the length thereof. The implant devices of the present invention are designed to facilitate spinal support while allowing interchangability of components to thereby reduce implant costs and are also designed to reduce compression stress to the spinal column to thereby alleviate the possibility of neurologicly adverse affect to the medulla of the spine, such as disc compression or cutting off blood supply through the spinal column and thereby eliminates the chance for patient paralysis.

2. History of the Related Art

Scoliosis is a disease which mainly appears in young children during their growth years and the cause of which is unknown. The disease causes a normal spine to twist around itself and bend towards one of the sides and at the same time towards the front or back of a patient. In this respect, scoliosis is a tridimensional deformity of the spine which requires that any type of implant device be capable of correcting or normalizing the proper spinal alignment not only in the frontal plane, but also in the sagittal and axial planes of the patient's back.

Mild scoliosis may be treated by the use of special braces which can be worn exteriorly, however the disease can reach magnitudes which require surgical implantation of frames or braces to realign the vertebrae of the spine.

Early implantation devices incorporated a generally round stainless steel bar which was placed along the length of the spine to which the vertebrae were tied in order to correct the alignment of the vertebrae along the frontal plane. Although this type of device gained early acceptance it did not correct the total problem with spinal alignment as it did not deal with the sagittal and axial deviations of the spinal column.

Subsequent implant devices were developed which introduced the use of sublaminar wiring which incorporated stainless steel wires which passed through the back part of each vertebrae and which were then tied to two L-shaped stainless steel rods placed on either side of the spine. This type of device had the additional advantage of providing lateral compression and improved correction in the frontal plane. Unfortunately, this type of device does not provide sufficient stability and thus have not been widely accepted. Further development led to the formation of a rectangular rod-like frame to which the steel wires could be attached. This type of device had the effect of stabilizing the ends of the rods and therefore formed a more rigid structure. Unfortunately, when the length of the rods became excessive the rods themselves, which extend along the length of the spine, would have a tendency to collapse towards one another along their intermediate length thereby reducing the effectiveness of the device during patient treatment.

Further developments were made in spinal implantation devices such as disclosed in U.S. Pat. No. 4,686,970 to Dove et al.. This type of device modified the rectangular frame so as to provide generally V-shaped cross members for connecting the bars which extend along a patient's spine. With the device, wire ties were utilized to secure the vertebrae to the corners of the wire frame with the wires being directed to the corners by the tapered V-shaped cross members. Unfortunately, this type of structure has not proven to be sufficiently rigid to allow the best correction of the deformity and because that when the bar elements exceed a predetermined length it is possible for the side bars to collapse relative to one another during patient treatment. Further, during patient treatment it has been noted that in some instances the use of V-shaped cross members at the level of the thoracic spine produce a sensitive protruding lump under the skin that is not always well tolerated. Rigidity of an implant device is a desired property that will facilitate the correction of the deformity but reposition of the deformed spine to its normal position can lead to crimping of the vertebrae against each other forcing the spinal disc to protrude.

Dove et al. also discloses a modified device for treating children during their growth years. The modified device includes a frame-like member which is extensible in two sections so that the frame would theoretically lengthen as the length of the spinal column of the patient grew during the patient's growth years. Unfortunately, this type of device has not proven effective as body tissues adhere to both of the telescoping portions of the frame thereby prohibiting any spontaneous telescoping movement once the device has been implanted for any significant period of time. Further, even if movement was allowed, the movement is unrestricted between the two ends of the interfitting frame members. Undesirable movement of the frame members could result in shifting of the frame elements along the longitudinal axis of the spine with such shifting thereby allowing the collapse of the corrected spine.

Further improvements have been made in spinal implant devices and are disclosed in U.S. Pat. Nos. 4,738,251 issued Apr. 19, 1988 and entitled Correcting Devices for Spine Pathology and 4,875,471 issued Oct. 24, 1989 and entitled Device for Correcting Deformities of the Spine, both issued to the applicant of the present invention. In the earlier patent a device was disclosed which included a pair of elongated rod-like members which extended along the length of the deformed portion of the spine and which were connected by curved end portions which were designed to define a radius of curvature continuously from end-to-end and which therefore differed from the V-shaped cross members which were utilized in the Dove et al. patent. The implant device further included outwardly extending hook members which were positioned along each of the cross members and along each of the side rod members adjacent each cross member for purposes of facilitating the anchorage of stainless steel wires utilized to secure the vertebrae to the frame of the implant device. In the latter patent it was recognized that when spacer members were only provided adjacent the ends of the elongated rod members which extended along the deformed length of the patient's spinal column that the rods would tend to collapse relative to one another thereby not providing proper support for the vertebrae which were tied to the implant frame. Therefore, it was recognized that at specifically spaced points it was necessary to provide arcuate intermediate spacer members to thereby reinforce the elongated rod members to provide a more rigid overall structure. With this device, the frame is reinforced and is rigid in the frontal plane of the patient's spinal column, however the frame may be bent utilizing specially designed tools to reproduce the physiologic curves of the sagittal plane of the patient's spinal column. Thereafter, the frame may be progressively wired to the spine in such a manner that the wires interact with the frame so that the frame and wires concurrently react to correct the tridimensional deformity of the spine. Utilizing the implant device disclosed in U.S. Pat. No. 4,875,471 the curved cross or spacer members which join the elongated bar members of the implant frame effectively retain such bars in parallel relationship along their entire length thereby reinforcing the angle of correction of the spine in the sagittal plane. Further strength is imparted to the frame by forming the elongated rod members with a rectangular cross section as opposed to a round cross section as was traditionally utilized in implant frames.

Unfortunately, although the prior structures developed by the applicant of the present invention are believed to be significant advances in spinal implant technology, it has been recognized that such implants have features which limit their applicability. Generally, implant frames have not been designed to permit realignment of their reinforcing members during surgery, thus allowing the reinforcing strength of the spacer or cross members to be selectively applied at various points along the length of the implant frames. Thus, when rigid frames having rigid cross pieces are applied it is possible that the vertebrae may be drawn into a compact relationship with respect to one another due to the fixed components of the frame member. That is, when the spinal column is attached so that the normal vertebrae on either side of the deformed spinal section are wired to the endmost cross members associated with a rigid frame, the deformed vertebrae and disc which are intermediate must collapse into a linear space defined by the length of the frame. However, the spine itself is generally arcuately curved and therefore defines a dimension which is greater in length than the length defined by the frame. Should the vertebrae and disc become compressed it is possible that the disc space could close too much and cutoff blood supply by compression of the medulla. Such a cutoff of blood supply can result in patient paralysis.

A further disadvantage of prior art spinal implant frames is that they are extremely expensive to produce as each rigid frame must be manufactured in given dimensions i.e. lengths and/or widths, depending upon the size of the patient to be treated. Currently, there may be as many as 43 models of a given implantation frame which must be chosen to suit patients Again, as the frames are not adjustable, separate frames must be retained in inventory thereby significantly increasing treatment costs This procedure is further complicated in that an additional set of 43 models are provided for children. Therefore, prior art implants have not been designed to be universally applied nor have not been designed to allow the interchange of components so as to facilitate the formation of a rigid frame for each patient.

An additional example of prior art spinal implantation device is disclosed in Soviet Union patent 1063404 of Dec. 30, 1983.

SUMMARY OF THE INVENTION

This invention is directed to an adjustable spinal implant frame utilized in the treatment of scoliosis which includes a pair of elongated rod-like members which are preferably of oblong cross section and which are united at spaced intervals by arcuately shaped cross or spacer members which are utilized to retain the rod members substantially parallel. In the preferred embodiment, each of the spacer elements associated with the frame is designed to be adjustably oriented with respect to the rod-like members with each spacer member including a pair of generally open sockets which encircle the rod members and through which locking screws are threadingly received. Each of the socket members is connected by an arcuate link which is integrally formed or secured thereto. In some embodiments, it may be necessary to provide only the uppermost spacer member with the adjustable features utilizing fixed spacer members along the remaining length of the implant frame.

In an additional embodiment of the present invention, the adjustable spacer or cross members include spaced socket members having an opening defined therethrough which is of a diameter which is slightly greater than the dimension of the elongated rods associated with the implant frame. Further, each of the socket members is designed to be relatively short from end-to-end thereby extending along a very short portion of the length of the rod members. The oversized openings in the sockets are designed to allow the reinforcing members to be slidable along the elongated rods even after such rods have been bent so as to be configured with the natural curvature which is to be achieved of the patient's spinal column. In this manner, an implant frame is provided where the spacer members may be selectively placed to provide appropriate reinforcement of the frame even in those areas where the rod members of the frame are bent or curved.

It is a primary object of the present invention to provide an implant frame for use in treating scoliosis and other spinal deformities wherein the frame is reinforced by a plurality of spacer or cross members at least one of which is adjustable so that the length of the frame, as defined between the endmost spacer members, may be adjusted so as to permit an elongation of the frame to thereby accommodate the length of the patient's spinal column which prior to treatment may be longer than the frame due to the arcuate configuration of the spine so that as the spinal vertebrae are tied to the frame the length of the frame may be increased to prevent compression of the patient's vertebrae and discs.

It is also an object of the present invention to provide an implant frame which is adjustable during implantation but wherein the frame members may be locked to provide a rigid structure which will not allow any shifting of the components of the frame following implantation to thereby provide a structure which will accommodate realignment of the patient's spinal column without the application of adverse compression thereby reducing the risk of patient paralysis through a cutoff of blood supply through a patent's spinal column.

It is yet a further object of the present invention to provide a spinal implantation device wherein the elongated bars associated with each frame may be selectively chosen for a given patient and thereafter joined by separate lockable cross or spacer members which may be universally applied to any length of elongated rod members so that the components of the frame may be selectively utilized to structure any given length of frame required without having to have the frame manufactured in specific and varied sizes.

It is also an object of the present invention to provide an implantation device for treating deformities of the spine wherein the components thereof may be separately manufactured and assembled by the surgeon to define a given shape or configuration as required to treat a given patient thereby allowing a universal application to the parts and thus reducing the cost in manufacture and increasing the availability of the implantation device to those who otherwise may not be able to afford such devices for proper medical treatment.

It is yet another object of the present invention to provide an implantation device for treatment of spinal deformities wherein the elongated rod members utilized to rigidly support the spine on either side thereof are joined by adjustable spacer or cross members having socket portions which encircle the rod shaped members which socket portions are designed to permit the spacer members to slide along curved segments of the elongated rods so that the reinforcement of the rods may be provided along not only the straight portions thereof but along the curved portions thereof.

BRIEF DESCRIPTION OF THE DRAWINGS

FIG. 1 is an illustrational view of a patient's spinal column which is deformed from the natural line of curvature indicated along line B, with the deformed configuration being indicated by line A.

FIG. 2 is an illustrational view of a prior art implantation device showing the upper and lower vertebrae adjacent to the deformed portion of the spine being secured thereto by stainless steel wire ties and illustrating that the overall length of the improperly curved portion of the spine is greater than the length of the overall implantation device.

FIG. 3 is an illustrational view of the prior art device of FIG. 2 showing the vertebrae tied to the implantation frame with the vertebrae being caused to be compressed relative to one another as they are brought into alignment along the line B illustrated in FIG. 1.

FIG. 4 is a perspective view of the implantation device of the present invention.

FIG. 5 is an enlarged cross-sectional view taken along lines 5—5 of FIG. 4 and showing one of the reinforcing cross members of the present invention.

FIG. 6 is a top plan view of FIG. 5.

FIG. 7 is an illustrational view of the implantation device of the present invention showing the upper and lower vertebrae adjacent the deformed portion of a spinal column being attached by wires to the endmost cross members of the device.

FIG. 8 is an illustrational view of the device shown in FIG. 7 wherein the uppermost spacer or cross member is shown as being adjustably extended to compensate for the overall length of the deformed portion of the spinal column and allowing for proper spacing of the vertebrae relative to one another as each vertebrae is wired to the implantation frame.

DESCRIPTION OF THE PREFERRED EMBODIMENT

Figure 9:
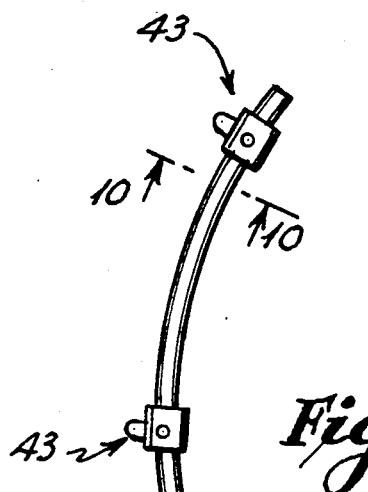
FIG. 9 is a side elevational view of a second embodiment of the present invention wherein the frame has been bent to conform to the natural curvature of a patient's spine.

With continued reference to the drawings, in FIG. 1 there is shown a portion of a patient's spinal column which has been deformed due to scoliosis to a point which it is no longer possible to treat the patient utilizing exterior braces and thus requiring the implantation of a surgically placed stabilization frame to which the vertebrae of the spinal column may be wired in a manner such as disclosed in applicant's previous U.S. Pat. No. 4,875,471 the contents of which are incorporated herein by reference. Likewise, incorporated herein by reference is U.S. Pat. No. 4,738,251 also the applicant of the present invention.

It will be noted in FIG. 1 that the deformity of the patient's spinal column has resulted in the vertebrae "V" being disposed along an arcuate line of curvature indicated at A. In order to correct the deformity it is necessary that the vertebrae be aligned as shown in line B. Due to the need to realign the vertebrae the vertebrae if fixed from end-to-end must be compressed as the linear distance defined by arc A is greater than the distance defined by line B.

With respect to FIGS. 2 and 3, a prior art reinforced implant frame such as disclosed in U.S. Pat. No. 4,875,471 is disclosed wherein the upper and lower normal vertebrae "V" are shown as being tied by stainless steel wires "W" to the upper and lower cross members 20 of the frame 21. The frame also includes intermediate reinforcing or cross members 22 spaced along the length of the elongated rods 23 and 24 of the frame. As shown in FIG. 3, the vertebrae are compressed linearly due to the fixed length of the frame 21. This could possibly result in compression of the discs between the vertebrae and thereby adversely effect blood supply through the patient's spinal column.

With particular reference to FIGS. 4-6, the improved spinal implant frame 30 of the present invention will be disclosed in greater detail. The implant frame includes a pair of elongated rod members 31 and 32 which are disposed generally parallel with respect to one another and which are reinforced and connected by a plurality of reinforcing spacing members 33. In order to increase the strength of the rod members 31 and 32, they are preferably formed with a somewhat rectangular or oblong configuration as best shown in cross section in FIG. 5. However, in some instances, round configurations or other configurations may be utilized as well.

Each of the rod elements 31 and 32 and the reinforcing cross members 33 are preferably formed of a material which is suitable for human implantation and in the preferred embodiment is stainless steel. The length of each of the rod member 31 and 32 will vary depending upon the exact nature of deformity being treated and the size of the patient. Likewise, the spacing between the rod members will vary depending upon the size of the patient.

The reinforcing members 33 shown in FIG. 4 are each designed to be adjustably moved along the length of the rod members 31 and 32. However, in some instances, it may be necessary to provide for the movement of only one or more of the members, in particular the uppermost reinforcing spacer member 33'. Each spacer member includes a pair of tubular socket portions 34 and 35 which are joined by an arcuate link 36. The arcuate portion 36 should be defined by a generally continuous arc having an enlarged radius of curvature which is preferably defined by an arc of a circle having a radius greater than the distance between the rod members. It is preferred that the curvature be such as to substantially accommodate the anatomy of the posterior spine. Therefore, the radius of curvature of the link 36 will be different for cervical vertebrae than for thoracic or lumbar vertebrae. It is, however, desired to ensure that the links 36 do not take on the configuration of a V-shaped connector in order to ensure that proper strength is imparted to the member and also to prevent adverse effects of the member with respect to the patient's body or skin after the device has been implanted.

Each spacer member is shown as also including a pair of lock nuts or set screws 37 and 38 which extend through each of the sockets 34 and 35 and which are utilized to lock the spacer members to the rod members 31 and 32. A special wrench or other tool may be utilized to adjust the lock nuts 37 and 38 as is necessary. It should be noted that the lock nuts are generally spaced out of alignment of an axis taken along the length of the arcuate portion 36 to thereby provide outer projections which may be utilized when tying stainless steel wire around the curved arcuate portions 36 and the outer portion of the sockets. In this manner, the lock nuts will function as the hook members which are disclosed in applicant's U.S. Pat. No. 4,875,471. Due to their adjustability, the spacer members may be applied or aligned at any point along the length, the rod members 31 and 32. In this manner, the overall frame 30 may be reinforced at any desirable point along the length of the implant frame 30. In addition, the adjustability of the cross members allows for the members to be momentarily shifted during surgical implantation to thereby facilitate the tying of the members to the vertebrae in a manner as discussed in applicant's previous patents, referenced hereinabove.

With particular reference to FIGS. 7 and 8, in use of the spinal implant 30 of the present invention, just prior to implantation surgery the frame is maintained straight in a frontal plane but may be bent in a sagittal plane with instruments specially designed for that purpose. For scoliosis patients, the elongated rod members 31 and 32 normally remain substantially in parallel relationship, however, for kyphosis and lordosis patients, the parallel rod members 31 and 32 are curved as necessary to correct the misalignment of the spine in the sagittal plane. The implantation device is thereafter attached initially to the spine by wiring the two normal vertebrae "V" which are adjacent to the ends of the deformed curvature of the spine, one will be to the more caudal and the other to the more cephalic. These two vertebrae are secured to the lower and uppermost reinforcing spacer members 33 and 33'. Unlike prior art implantation devices, the implantation device of the present invention is designed to permit a sliding adjustment of the reinforcing spacer members and therefore at least one of the spacer members 33 or 33' should be somewhat loosely mounted to the elongated rod members 31 and 32. In FIG. 7, the set screws or lock nuts 37 and 38 of the spacer member 33' are loosely adjusted to permit a sliding movement of the spacer member relative to the rod members 31 and 32, while the set screws or lock nuts of the lower spacer member 33 are tightly engaged with the rod members 31 and 32 to thereby rigidly lock spacer member 33 in fixed relationship with respect thereto Thereafter the vertebrae are continuously drawn toward the rod members 31 and 32 and each vertebra tied to the frame as shown in FIG. 8 progressively from the lowermost towards the uppermost vertebra of the deformed spine. As the vertebrae are progressively wired to the frame the intermediate spacer members may be adjusted as necessary to allow for reinforcement of the rod members 31 and 32 at proper locations to provide maximum rigidity of the frame. These members are thereafter secured by tightening their lock nuts 37 and 38 to the rod members 31 and 32. As the uppermost spacer member is free to move along the rod members 31 and 32 as the deformed portion of the spine is tied to the frame the uppermost spacer member will progressively be shifted along the rod members 31 and 32 thereby preventing compression of the deformed portion of the spinal column during the implant procedure. Once the vertebrae have been wired to the frame 30 the uppermost spacer member 33' is secured in locked and rigid relationship with respect to the rod members 31 and 32 by adjustment of the lock nuts 37 and 38.

Figure 10:
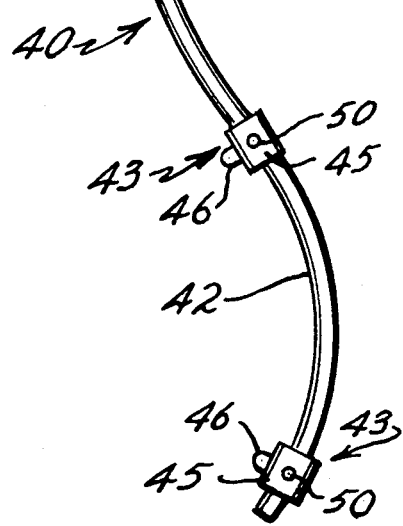
FIG. 10 is an enlarged cross-sectional view taken along lines 10—10 of FIG. 9 showing a spacer member having enlarged socket portions to permit the spacer member to be slidingly adjustable along the length of the curved segments of the rod members of the embodiment invention shown in FIG. 9.
Figure 11:
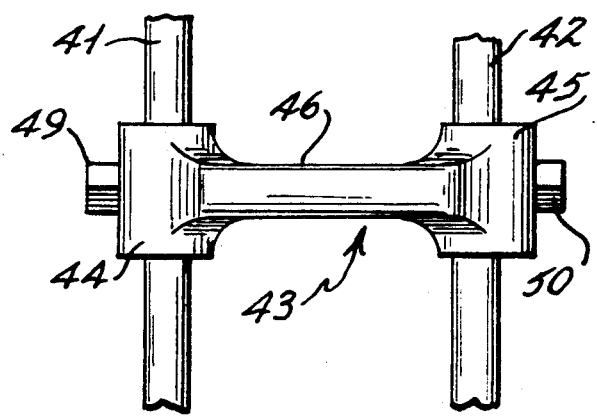
FIG. 11 is a top plan view of the spacer member shown in FIG. 10.

With specific reference to FIGS. 9-11, a modified embodiment of the present invention is disclosed in greater detail. In this embodiment, the elongated rod members 41 and 42 are shown as being curved along their length yet remain parallel with respect to one another. The frame 40 is designed for correction of thoracic lordosis or flat back syndrome. Due to the curvature of the rod members 41 and 42 it is necessary that the spacer members, herein designated at 43, be capable of being slidingly adjusted along the arcuate segments of the rod members 41 and 42. In order to accomplish this each of the spacer members 43 is provided with a pair of spaced socket members 44 and 45 which are interconnected by arcuately curved portions 46 which are curved as was previously discussed with respect to the embodiment shown in FIGS. 4-8. The openings 47 and 48 through the socket members 44 and 45 are of a greater diameter than the cross-sectional dimension of the rod members 41 and 42 thereby establishing a clearance between the walls defining the openings and the exterior surface of the rod members and thus allowing a limited degree of movement between the spacer members and the rod members. This spacing between the socket members and the rod members will allow the socket members to be slidingly moved along the arcuate portions of the rod members 41 and 42. To further assist in the movement of the spacer members and as shown in FIG. 11, the socket members have been shortened from end-to-end as compared with the spacer members of the initial embodiment thereby further increasing the adjustable capability along curved segments of the rod members 41 and 42. As with the initial embodiment lock nuts 49 and 50 are provided for locking the spacer members with respect to the frame 40 at a preselected or adjusted position.

In view of the foregoing, it is noted that the adjustable spinal implant of the present invention not only allows for adjustment of the reinforcing spacer members during implantation but the interchangability of the components i.e. the rod members and the spacer members permit a more universal application of the implantation device to various patients. That is, the spacer members 33, 33' or 43 may be used interchangeably with rod members 31 and 32 or 41 and 42 with the rod members being selected of varying lengths depending upon the exact nature of the patient deformity and the size of the implant. The interchangability of the components will allow a reduction in manufacturing and material cost which will be of extreme benefit in reducing overall cost of patient treatment.

I claim:

1. A spinal implant device comprising an adjustable frame defined by a pair of elongated rod members which are oriented generally parallel with respect to one another and having upper and lower ends, said rod members having an outer sliding surface being smooth and continuous from said lower to said upper ends, a plurality of reinforcing spacer members spaced along said rod members and having outer ends which are secured to said rod members, each of said spacer members including an arcuate portion which extends between said outer end portions and outwardly with respect to a plane defined by said rod members, at least one of said spacer members being continuously slidingly adjustable in either direction along at least a portion of the length of said rod members and said outer ends thereof defined by generally open sockets of a size to slidingly receive said rod members therethrough, and locking means for locking said at least one spacer member in fixed non-sliding relationship with respect to said rod members at any selected position relative to said at least a portion of the length of said rod members.

2. The spinal implant device of claim 1 wherein said at least one spacer member is positioned adjacent said upper ends of said rod members, and a lowermost of said spacer members positioned adjacent said lower end of the said rod members.

3. The spinal implant device of claim 2 including a plurality of intermediate spacer members disposed in spacer relationship between said at least one and said lower spacer members, said outer ends of each of said intermediate and lowermost spacer members including an open socket through which said rod members are extended so that said intermediate and lowermost spacer members are selectively and continuously adjustable with respect to the length of said rod members, and locking means for locking each of said intermediate and said lowermost spacer members to said rod members at any selected position relative to said at least a portion of the length of said rod members.

4. The spinal implant device of claim 3 in which said rod members have oblong cross-sectional configurations.

5. The spinal implant device of claim 4 in which said locking means for locking said spacer members to said rod members include screw threaded means extending through each of said outer end portions and into said sockets.

6. The spinal implant device of claim 4 wherein said rod members include curved segments along the length thereof, said sockets defining openings therethrough of a first dimension and said rod members have cross sections defining a maximum second dimension, said first dimension being greater than said second dimension to an extent to allow said spacer members to be slightly pivoted with respect to each of said rod members whereby said spacer members may be slidingly adjustable along said curved segments of rod members.

7. The spinal implant device of claim 6 in which said locking means extend outwardly with respect to said socket members to provide protrusions around which wire ties may be secured and, said protrusions being spaced from said arcuate portion of said spacer members.

8. The spinal implant device of claim 1 wherein each of said rod members has a generally oblong cross-sectional configuration.

9. The spinal implant device of claim 1 wherein each of said spacer members is continuously adjustable with respect to the length of said rod members, each of said end portions of said spacer members including open sockets of a size to loosely receive said rod members therein, locking means extending through each of said socket members so as to be selectively engageable with said rod members within said sockets, and said locking means extending outwardly with respect to said socket member so as to provide a protrusion around which a wire tie may be supported when said implantation device is in use.

10. The spinal implant device of claim 9 in which said arcuate portion of each spacer member is defined by an arc of a circle having a radius greater than the distance between said first and second rod members.

11. A spinal implant device comprising an adjustable frame defined by a pair of elongated solid rod members which are oriented generally parallel with respect to one another and having upper and lower ends, said rod members having an oblong cross section and outer sliding surface, a plurality of reinforcing spacer members spaced along said rod members and having outer ends, each of said spacer members including an arcuate portion which extends between said outer end portions, said spacer members being continuously slidingly adjustable in either direction along at least a portion of the length of said rod members and having outer ends defined by generally open sockets of a size to loosely and slidingly receive said rod members therein, and locking means extending through each of said outer end portions and into said open sockets for selectively engaging said rod members after said spacer members in non-sliding relationships have been moved to an adjusted position relative to said rod members.

12. The spinal implant device of claim 11 wherein said rod members include curved segments along their length, said sockets being of a size to permit said spacer members to be freely slidable relative to said curved segments.

* * * * *